United States Patent [19]

Hanotier et al.

[11] 4,390,472

[45] Jun. 28, 1983

[54] PROCESS FOR THE OXIDATION OF HYDROCARBONS

[75] Inventors: Jacques D. V. Hanotier; Monique J. S. Bridoux, both of Lasne-Chapelle-Saint-Lambert; Jacques F. Dauby, Groot-Bijgaarden, all of Belgium

[73] Assignee: Labofina S.A., Brussels, Belgium

[21] Appl. No.: 256,255

[22] Filed: Apr. 22, 1981

[30] Foreign Application Priority Data

Apr. 29, 1980 [LU] Luxembourg ............................ 82414

[51] Int. Cl.³ .......................... C07C 53/00; C04B 9/02
[52] U.S. Cl. ..................................... 260/398.6; 208/3; 106/14.28
[58] Field of Search ........................ 260/398.6; 208/3; 106/14.28

[56] References Cited

U.S. PATENT DOCUMENTS

| | | | |
|---|---|---|---|
| 1,981,384 | 11/1934 | Friedolsheim | 260/398.6 |
| 2,184,952 | 12/1939 | Zimmer | 260/398.6 |
| 2,330,525 | 9/1943 | Shields | 260/398.6 |
| 2,522,678 | 9/1950 | Kozacik | 260/398.6 |
| 2,818,419 | 12/1957 | McKinley | 260/398.6 |
| 3,224,956 | 12/1965 | Phillips | 228/3 |

Primary Examiner—John F. Niebling

[57] ABSTRACT

The process for the catalytic oxidation of hydrocarbons and more particularly of petrolatum of similar raw material having a high content in microcrystalline waxes comprises introducing a molecular oxygen-containing gas into melted petrolatum in the presence of a usual oxidation catalyst and in the presence of water, which is used in an amount comprised between about 1% and 25%, based on the weight of petrolatum.

The acid products resulting from this oxidation reaction and their calcium soaps are anti-rust compounds.

9 Claims, No Drawings

PROCESS FOR THE OXIDATION OF HYDROCARBONS

This invention relates to a process for the partial oxidation of hydrocarbons by molecular oxygen. It relates more particularly to the partial oxidation of hydrocarbon mixtures, such as petrolatum waxes, which are contained in normally solid or semi-solid petroleum waxes.

The acid organic products resulting from this oxidation have various uses. In particular, they can be transformed into calcium soaps which are the active components of rust preventive coatings. However, the acid products prepared by oxidation of petroleum waxes must meet some requirements when they are used to the production of effective coatings at low cost. For instance, the acids must be produced with high yields from raw materials which are readily available and at low price. Moreover, the calcium soaps of these acids must be fairly soluble in solvents, such as white spirit. Furthermore, the coatings must have an adequate fluidity so that they can be easily applied by means of a spray nozzle to the metallic surfaces to be protected, such as the inner parts of car doors or other enclosed areas of a car body where spot welding and crimping during assembly can leave the steel sheet naked at points which are no longer accessible for painting and which require therefore a protective coating. After evaporation of the solvent, the coating must form a waxy film which provides an effective protection against corrosion and which retains its plasticity at temperatures as high as 80° C. or even more.

The known processes for producing acid products do not meet the above requirements. By way of example, acids which are produced from some easily oxidizable raw materials form calcium soaps which provide a fairly feeble protection and which are not very soluble in white spirit and similar solvents. On the other hand, valuable calcium soaps can be produced from some other raw materials, but the latter are not easily oxidized. Microcrystalline waxes, also known as petrolatum, are examples of such raw materials. Even when these waxes are free from oxidation inhibitors, the oxidation rate falls down rapidly and the reaction does not reach the wanted oxidation level. The exact nature of this problem is not known, but it appears that there is a correlation between the difficulty encountered for oxidizing petrolatum-like materials and their content in aromatic components. A proof is given by the fact that this problem does not occur in case of oxidation of vaselines which are produced by refining petrolatum.

There is thus a need for an oxidation process according to which petrolatum-like materials are easily oxidized to acid products whose calcium soaps meet the above mentioned requirements, said oxidation being carried out without resorting to a prior purification or dearomatization of these raw materials.

It is an object of the present invention to provide such an improved process. Another object of this invention is to provide a process for the oxidation of petrolatum which does not need the use of promoters or other additives.

The process of this invention for the oxidation of petrolatum to acid products comprises introducing of molecular+oxygen-containing gas into melted petrolatum in the presence of an oxidation catalyst and in the presence of water in an amount comprising between about 1 and 25% baed on the weight of petrolatum.

The process can be applied for the oxidation of any petrolatum wax, but is particularly suitable for the oxidation of petrolatum, which is a raw material with a high content in microcrystalline waxes containing mainly saturated aliphatic hydrocarbons $C_{34}H_{70}$ to $C_{43}H_{88}$. Petroleum is obtained when lubricating oils are refined by extraction or by recrystallization at low temperatures of heavy cuts of petroleum. This raw material is therefore readily available at low cost. The acid products prepared by oxidation of petrolatum can be transformed into calcium soaps which exhibit a noticeable anti-rust action. But, up to now, this advantage was unfavorably balanced by the fact that the known oxidation methods do not permit easy oxidation of petrolatum.

However, it has been unexpectedly found that petrolatum was easily and rapid oxidized by adding a sufficient amount of water. Satisfactory results have been obtained when the amount of added water is about 1% based on the weight of petrolatum. On the other hand, there is no advantage in using amounts of water higher than about 25%, the presence of a too large amount of water reducing the production capacity of the reactor. Generally, the amount of water ranges between 2% and 20%, and more particularly between about 5 and 10%, based on the weight of petrolatum. In order to maintain this amount of water in the reaction system during the oxidation, the vapors carried along with the vent gas and containing mainly steam are condensed and refluxed. Another means comprises withdrawing this condensate and progressively introducing fresh water as a substitute into the reactor. This latter method is more advantageous, because the lower acids (formic and acetic acids) produced in substantial amount as oxidation by-products and which are detrimental to the reaction are removed from the reaction system. Indeed, they form a diluted aqueous solution in the condensation step. It is easy to dispose of this solution and therefore to solve the evaporation problem.

The oxidation reaction is carried out at a temperature which is generally ranging between about 120° and 190° C. Below about 120° C., the oxidation rate is too low. On the other hand, working above about 190° C. generally results in overoxidation with formation of large amounts of by-products, such as lower aliphatic acids. The oxidation reaction is exothermic and it is required to employ any known means to keep the reaction temperature between the above mentioned limits. A further advantage of the process of the present invenvtion is the ease with which temperature control can be achieved; owing to the presence of water in the reaction system, the heat evolved from the oxidation can be easily be removed by controlled vaporation of water.

The catalyst used in the process of the invention may be a salt of any heavy metal conventionally employed in the oxidation of hydrocarbons in liquid phase provided that it is soluble or forms a soluble compound in the reaction mixture. Salts of aliphatic acids, such as the acetates, propionates, sterates or naphthenates of hevy metals, more particularly cobalt and manganese are generally used. Mixtures of cobalt salts and manganese salts are particularly active catalysts. The amount of catalyst may vary between the wide limits, but generally, preferably ranges from about 0.05% to about 2.0%, based on the weight of petrolatum.

In carrying out the oxidation process of the present invention, the mixture or petrolatum, water and catalyst is heated while a molecular oxygen-containing gas is passed through the mixture. This gas is homogeneously dispersed and an efficient stirring of the reaction mixture is provided so as to ensure intimate contact between the different components and to avoid decantation of the system in two separated liquid phases. The oxygen-containing gas is generally air, but air enriched with oxygen or even pure oxygen may be used.

The pressure at which the oxidation reaction is carried out depends on the temperature. The pressure must be high enough so as to maintain the main part of water in the liquid phase during the reaction. Moreover, the dissolution of oxygen into the petrolatum and the reaction rate are improved when the pressure is high. This pressure may reach 60 kg/cm$^2$. However, high pressures mean high investment costs. Accordingly, the pressure is generally from about 10 to 25 kg/cm$^2$.

The process of this invention may be carried out as a continuous flow process, but generally a batchwise process is used. The raw petrolatum is oxidized up to formation of an oxidation product having the wanted acid number (acid number=number of milligrams of KOH which is needed to neutralize 1 g of the oxidation product). The reaction mixture is then cooled to a temperature of 80°-90° C., the introduction of oxygen is discontinued and the pressure is released. The aqueous phase containing the major part of the catalyst is withdrawn. When the reaction is carried without reflux of the vapors carried along with the vent gas, the withdrawn aqueous phase contains only a minor part of the lower acids which are by-products of the reaction. Therefore, the aqueous phase may be used again for a further oxidation reaction. The problem of waste waters containing heavy metals is thereby solved.

When the aqueous phase has been withdrawn, the oxidation product can be recovered. Although this oxidate has antirust properties and may be used as protective coating, it is preferred to transform at least a part of the acids contained in this oxidate into calcium soaps, in order to improve its thermal stability. The saponification reaction is preferably carried out after dilution of the oxidate with the solvent, such as white spirit, generally used for the production of the rust preventive coating.

The present invention is illustrated by the following Examples:

EXAMPLE 1

The viscosity of the used raw petrolatum was 20.39 cSt at 210° F. and 35.82 at 80° F. (ASTM D.445). Its melting range was 55°-65° C.

Into a stainless steel reactor equipped with a heating jacket, a cooling coil, a stirrer, a gas inlet tube and a vent connected to a reflux condenser, there was charged (parts by weight):

| | |
|---|---|
| raw petrolatum | 100 parts |
| water | 5 parts |
| cobalt naphthenate (at 10% by wt of metal) | 0.5 |
| manganese naphthenate (idem) | 0.5 |

The reactor was pressurized with air up to 20 kg/cm$^2$ and air was admitted at a flow rate of 100 liters per hour, while the charge was heated by circulating heated oil into the jacket. As the temperature reached about 125° C., the oxidation reaction started rapidly, as shown by the sharp decrease of oxygen content in the vent gas. The temperature then increased rapidly and was maintaned at about 150° C. by controlled cooling. From this moment, the oxygen absorption rate was practically constant. After 2 hours, the reaction was discontinued by cooling at 80°-90° C., the admission of air was stopped and the reactor was depressurized.

Afer sedimentation during 1 hour, the lower aqueous phase containing the major part of this catalyst and of the lower acids was recovered. Thereafter the upper layer or organic phase was withdrawn. Its acid number was 41 mg KPH/g.

This oxidate was then diluted by a hydrocarbon solvent (white spirit) used in an amount (100 parts) equivalent to the amount of used petrolatum. Calcium hydroxide (5 parts) was added and the mixture was progressively heated up to 120° C. with elimination of the reaction water as formed. The obtained solution was cooled at about 90° C. and filtered at that temperature so as to remove the residual calcium hydroxide. The solution was further cooled at room temperature.

The obtained solution was practically free from sediment and remained stable even after a long storage. After spray application and evaporation of the solvent, a waxy and homogeneous film was formed.

The flow temperature of a film about 50 microns thick applied to a vertical steel panel and stoved for 1 hour (film previously dried for 24 hours at room temperature) was about 80° C. The anti-rust test as determined by the salt spray test (ASTM B.117; 5% NaCl, flow rate: 1.3 to 2.0 ml/h) has shown that the corrosion after 500 hours did not exceed 5% of the coated surface; this result was obtained without incorporation of additive improving the anti-rust properties of the coating.

EXAMPLES 2 to 4

The experiment of Example 1 was repeated, except that the amount of water was respectively 2, 10 and 20 parts for 100 parts of petrolatum, instead of 5 parts.

A comparative experiment was carried out under the same conditions, except that water was omitted in the mixture to be oxidized.

The obtained results are given in the following Table, together with the results of Example 1.

TABLE

| Example No. | Parts water per 100 parts petrolatum | Absorbed oxygen (liters/100 g Petrolatum) | | |
|---|---|---|---|---|
| | | 1st hr | 2nd hr | Total |
| 1 | 5 | 6.8 | 8.5 | 15.3 |
| 2 | 2 | 4.0 | 5.0 | 9.0 |
| 3 | 10 | 5.9 | 7.2 | 13.1 |
| 4 | 20 | 5.1 | 6.3 | 11.4 |
| Comparative | 0 | 3.1 | 0.6 | 3.7 |

The results show that in the absence of water in the charge, the reaction starts almost normally but the reaction rate falls down rapidly and is negligible during the second hour. This results is quite unexpected, more especially as water is produced during the oxidation. The oxidate of this comparative experiment was reacted with calcium hydroxide, as in Example 1, but the reaction product was slightly soluble in white spirit or similar solvents. After spray application, the film has a vaseline-like texture and its flow temperature was lower than 80° C.

By way of contrast, when water is added to the charge from the start of the reaction and in sufficient amount, the reaction progresses normally. The reaction rate increases progressively and tends to become stable at a value higher than the value reached at the start. The above given Table shows that the amount of added water is not critical. Amounts as high as 20% or even more may be used but the best results were obtained with an amount of water of about 5%.

What we claim is:

1. Process for the partial oxidation of hydrocarbons, more particularly of petrolatum or other material having a high content in microcrystalline waxes with formation of acid products, which comprises introducing a molecular oxygen-containing gas into melted petrolatum in the presence of an oxidation catalyst and in the presence of liquid water in an amount which is maintained between about 1% to about 25% based on the weight of petrolatum during the oxidation reaction.

2. The process according to claim 1, wherein the amount of water ranges from about 2% to about 20%, based on the wieght of petrolatum.

3. The process according to claim 2, wherein said amount of water ranges from about 5% to about 10%, based on the weight of petrolatum.

4. The process according to claim 1, wherein the oxidation reaction is carried out at a temperature comprised between about 120° and 190° C. and under a pressure between about 10 and 25 kg/cm$^2$.

5. The process according to claim 1, wherein the oxidation catalyst is a mixture of cobalt and manganese salts and is used in an amount ranging between about 0.05 and about 2.0%, based on the weight of petrolatum.

6. The process according to claim 1, 2, 3, 4, or 5 wherein the oxidation reaction is carried out as a batch process without refluxing the vapors carried along with the vent gas and the oxidized reaction system is separated into an aqueous phase and an oxidate.

7. The process of claim 6, further comprising the step of saponifying the oxidate.

8. The product made according to the process of claim 7.

9. A method of use of the product of claim 8 as a rust preventive coating.

* * * * *